US00PP22572P2

(12) United States Plant Patent
Ritchie

(10) Patent No.: US PP22,572 P2
(45) Date of Patent: Mar. 13, 2012

(54) ***COPROSMA* PLANT NAMED 'PLUM HUSSEY'**

(50) Latin Name: *Coprosma repens*
Varietal Denomination: Plum Hussey

(76) Inventor: John Stanley Ritchie, Otane Hawkes Bay (NZ)

( * ) Notice: Subject to any disclaimer, the term of this patent is extended or adjusted under 35 U.S.C. 154(b) by 0 days.

(21) Appl. No.: 12/927,898

(22) Filed: Nov. 29, 2010

(51) Int. Cl.
*A01H 5/00* (2006.01)

(52) U.S. Cl. ..... Plt./226

(58) Field of Classification Search ..... Plt./226
See application file for complete search history.

*Primary Examiner* — Kent L Bell

(57) ABSTRACT

A new cultivar of *Coprosma* plant named 'Plum Hussey' that is characterized by a compact habit and leaves that are yellow green when young and mature to dark red.

1 Drawing Sheet

Botanical classification: *Coprosma repens.*
Variety denomination: 'Plum Hussey'.

BACKGROUND OF THE INVENTION

The present invention relates to a new and distinct cultivar of *Coprosma* plant botanically known as *Coprosma* and hereinafter referred to by the cultivar name 'Plum Hussey'.

The new cultivar was discovered by the inventor as a single plant in a cultivated area of Otane, Hawkes Bay, New Zealand in 2007. 'Plum Hussey' was discovered in a commercial field of *Coprosma* plants. The exact parent plants are unknown.

Asexual reproduction by tip cuttings of the new cultivar 'Plum Hussey' was first performed in 2007 in Otane, Hawkes Bay, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Coprosma* cultivar 'Plum Hussey'.

1. *Coprosma* 'Plum Hussey' exhibits a compact habit.
2. *Coprosma* 'Plum Hussey' exhibits leaves that are yellow green when young and mature to dark red.

The closest comparison cultivars are *Coprosma* 'Karo Red' (not patented) and *Coprosma* 'Fire Burst' (U.S. Plant Pat. No. 14,906). The new cultivar 'Plum Hussey' is distinguishable from 'Karo Red' by the following characteristics:

1. 'Plum Hussey' has a taller overall height than 'Karo Red'.
2. 'Plum Hussey' has young leaves that are yellow green. The young leaves of 'Karo Red' are blue green.
3. 'Plum Hussey' has mature leaves that are dark red. The mature leaves of 'Karo Red' are orange red.

The new cultivar 'Plum Hussey' is distinguishable from 'Fire Burst' by the following characteristics:

1. 'Plum Hussey' has a taller overall height than 'Fire Burst'.
2. 'Plum Hussey' has young leaves that are yellow green. The young leaves of 'Fire Burst' are pink.

3. 'Plum Hussey' has mature leaves that are dark red. The mature leaves of 'Fire Burst' are red.

BRIEF DESCRIPTION OF THE DRAWING

The accompanying photograph illustrates the distinguishing traits of *Coprosma* 'Plum Hussey'. The plant in the photograph shows an overall view of a 24 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Coprosma* cultivar named 'Plum Hussey'. Data was collected in Cambridge, New Zealand from 24 month old outdoor grown plants in 2.5 liter containers. The time of year was Fall and the average temperature range was 18 to 25 degrees Centigrade during the day and 12 to 20 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Plum Hussey' has not been tested under all possible conditions and phenotypic differences may be observed with variations in environmental, climatic, and cultural conditions, however, without any variance in genotype.

Botanical classification: *Coprosma* 'Plum Hussey'.
Use: Ornamental perennial.
Parentage: The parents of 'Plum Hussey' are unknown.
Vigor: Moderate.
Growth rate: Moderate.
Growth habit: Freely branching, dense, bushy habit.
Plant shape: Broad upright inverted triangle.
Suitable container size: 2.5 liter container.
Height: Average 1.0 m in height.
Width: Average 1.0 m in width.
Hardiness: Tolerant to −3 degrees Centigrade.
Propagation: Tip cuttings.
Time to initiate roots: Approximately 20 days in the Summer and 25 days in the Winter.

Time to produce a rooted cutting: Approximately 40 days in the Summer and 200 days in the Winter.

Root system: Fine and fibrous.

Lateral branches:

*Dimensions.*—19 cm. in length and 3.5 mm. in diameter.

*Quantity.*—Approximately 20.

*Strength.*—Strong.

*Texture.*—Smooth.

*Color.*—197B.

*Internode length.*—1.6 mm.

*Pinching.*—Yes.

Foliage:

*Leaf shape.*—Obovate.

*Leaf apex.*—Obtuse.

*Leaf base.*—Rounded.

*Leaf length.*—Average 4.6 cm in length.

*Leaf width.*—3.4 cm in width.

*Pubescence.*—Absent.

*Leaf margin.*—Entire, slightly wavy.

*Leaf texture.*—Smooth, glossy (both surfaces).

*Vein pattern.*—Pinnate.

*Young leaf color* (*upper surface*).—144C.

*Young leaf color* (*lower surface*).—144C.

*Mature leaf color* (*upper surface*).—187C.

*Mature leaf color* (*lower surface*).—187C.

*Vein color* (*upper surface*).—144C.

*Vein color* (*lower surface*).—187C.

*Durability of foliage to stress.*—High.

Stipules.—Two stipules at leaf base, obovate in shape, 3.5 mm. in length and 2 mm. in width, color: 187D.

Flowers: Flowers have not been observed.

Disease and insect resistance: Plants of the new *Coprosma* have not been observed for disease or insect resistance.

The invention claimed is:

1. A new and distinct variety of *Coprosma* plant named 'Plum Hussey' as described and illustrated.

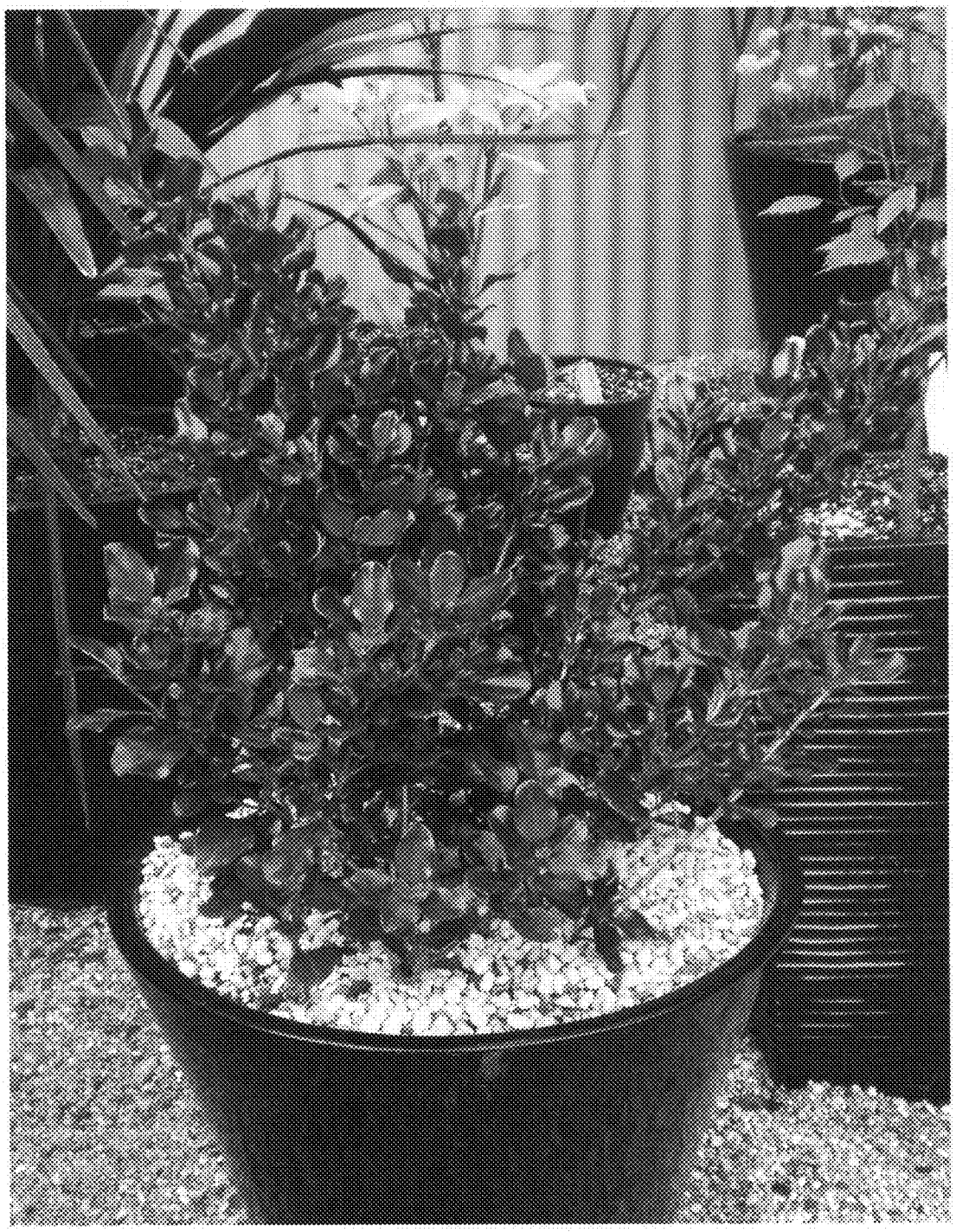

* * * * *